US010398373B2

(12) United States Patent
Nduka (10) Patent No.: US 10,398,373 B2
(45) Date of Patent: Sep. 3, 2019

(54) BIOFEEDBACK SYSTEM (71) Applicant: SENSE INNOVATION LIMITED, Brighton (GB)

(72) Inventor: Charles Nduka, Brighton (GB)

(73) Assignee: EMTEQ LIMITED, Brighton (GB)

(*) Notice: Subject to any disclaimer, the term of this patent is extended or adjusted under 35 U.S.C. 154(b) by 0 days.

(21) Appl. No.: 14/411,098

(22) PCT Filed: Jul. 1, 2013

(86) PCT No.: PCT/EP2013/063785
§ 371 (c)(1),
(2) Date: Dec. 23, 2014

(87) PCT Pub. No.: WO2014/005974
PCT Pub. Date: Jan. 9, 2014

(65) Prior Publication Data
US 2015/0157255 A1 Jun. 11, 2015

(30) Foreign Application Priority Data
Jul. 2, 2012 (GB) .................................. 1211703.2

(51) Int. Cl.
A61B 5/00 (2006.01)
A61B 5/0476 (2006.01)
(Continued)

(52) U.S. Cl.
CPC ............ *A61B 5/486* (2013.01); *A61B 5/0476* (2013.01); *A61B 5/0488* (2013.01);
(Continued)

(58) Field of Classification Search
CPC ...................................................... A61B 5/486
(Continued)

(56) References Cited

U.S. PATENT DOCUMENTS 6,097,981 A 8/2000 Freer
6,102,847 A 8/2000 Stielau
(Continued)

FOREIGN PATENT DOCUMENTS

EP 2602652 A1 6/2013
GB 2 396 421 A 6/2004
(Continued)

OTHER PUBLICATIONS

Facial Retraining, Bell's Palsy Information Site, http://www.bellspalsy.ws/retrain5.htm, 2006.*
(Continued)

*Primary Examiner* — Carl H Layno
*Assistant Examiner* — Dacheng Xie
(74) *Attorney, Agent, or Firm* — Kenealy Vaidya LLP (57) ABSTRACT Apparatus for providing muscular biofeedback, comprising: facewear supporting biosensors arranged such that, in use, the biosensors are situated for detecting activity of a predetermined set of facial muscles; a feedback unit for providing biofeedback to a wearer of the facewear; and a control unit coupled to the biosensors and the feedback unit and arranged to identify patterns in the signals from the biosensors characteristic of one or more predefined imbalances in muscle activity between the left and right sides of the face; wherein the control unit is configured to, on identifying a pattern in the signals from biosensors characteristic of a first predefined imbalance in muscle activity between the left and right sides of the face, cause the feedback unit to provide biofeedback in correspondence with the imbalance.

9 Claims, 2 Drawing Sheets (51) Int. Cl.
*A61B 5/0488* (2006.01)
*A61B 5/11* (2006.01)
*A61B 5/16* (2006.01)
*A61B 5/0484* (2006.01)

(52) U.S. Cl.
CPC ............ *A61B 5/1107* (2013.01); *A61B 5/165* (2013.01); *A61B 5/442* (2013.01); *A61B 5/6803* (2013.01); *A61B 5/0484* (2013.01); *A61B 2560/0238* (2013.01); *A61B 2562/0257* (2013.01)

(58) Field of Classification Search
USPC .................................................. 600/300–301
See application file for complete search history.

(56) References Cited

U.S. PATENT DOCUMENTS

| | | | |
|---|---|---|---|
| 6,402,520 | B1 | 6/2002 | Freer |
| 6,422,999 | B1 | 7/2002 | Hill |
| 6,626,676 | B2 | 9/2003 | Freer |
| 2006/0252979 | A1* | 11/2006 | Vesely ................. A61B 5/0482 600/27 |
| 2007/0060830 | A1* | 3/2007 | Le ....................... A61B 5/0476 600/544 |
| 2007/0179396 | A1 | 8/2007 | Le et al. |
| 2007/0276451 | A1 | 11/2007 | Rigaux |
| 2008/0218472 | A1 | 9/2008 | Breen et al. |
| 2009/0210028 | A1 | 8/2009 | Rigaux et al. |
| 2009/0214060 | A1 | 8/2009 | Chuang et al. |
| 2009/0309605 | A1 | 12/2009 | Prance et al. |
| 2010/0049278 | A1 | 2/2010 | Kuramori |
| 2011/0034912 | A1 | 2/2011 | De Graff et al. |
| 2011/0245702 | A1 | 10/2011 | Clark et al. |
| 2011/0288445 | A1 | 11/2011 | Lillydahl et al. |
| 2011/0313310 | A1 | 12/2011 | Tomita et al. |
| 2012/0029367 | A1* | 2/2012 | Hobeika ............ A61B 5/02416 600/500 |
| 2012/0029390 | A1* | 2/2012 | Colborn ............... A61B 5/0245 600/595 |
| 2012/0149467 | A1 | 6/2012 | Heck |
| 2012/0162598 | A1 | 6/2012 | Tsubota et al. |
| 2012/0229248 | A1* | 9/2012 | Parshionikar .......... G08B 21/06 340/3.1 |
| 2013/0123656 | A1 | 5/2013 | Heck |
| 2013/0324881 | A1 | 12/2013 | Kanoh et al. |

FOREIGN PATENT DOCUMENTS

| | | |
|---|---|---|
| WO | 91/13584 A1 | 9/1991 |
| WO | 2008/091323 A1 | 7/2008 |
| WO | 2008/109699 A2 | 9/2008 |
| WO | 2014/176420 A1 | 10/2014 |

OTHER PUBLICATIONS

Dimberg et al. Facial reactions to happy and angry facial expressions: Evidence for right hemisphere dominance, Phychophysiology (2000), p. 693-696.*

Carolyn Yucha et al.; "Evidence-Based Practice in Biofeedback and Neurofeedback"; applied psychophysiology & biofeedback; 2008 edition; ISBN 1-887114-19-X.

MyoTrac Infiniti; "The Complete Physical Therapy Solution"; Thought Technology Ltd.

International Search Report and Written Opinion of the International Search Report for PCT/EP2013/063785 dated Oct. 15, 2013.

P. Canavan, et al., 'Protocol for use of EMG and Tactile Biofeedback in Treatment of Temporomandibular Disorders and Myofacial Pain' Electromyography in Physical Therapy and Rehabilitation.

G. Geetha, et al., 'Noise Cancellation of Ocular and Muscular Artifacts from EEG Signals Based on Adaptive Filtering', International Journal of Computer and Electrical Engineering, vol. 4, No. 5, Oct. 2012.

P. Rani, 'Psychophysiology-Based Affective Communication for Implicit Human-Robot Interaction', 2005 Doctoral Dissertation, Vanderbilt University Nashville, TN, USA.

D. Kim, et al., 'Materials for stretchable electronics in bioinspired and biointegrated devices', Materials Research Society Bulletin, vol. 37, Mar. 2012.

Combined Search and Examination Report for GB1716430.2 dated Oct. 26, 2017.

* cited by examiner

BIOFEEDBACK SYSTEM

BACKGROUND OF THE INVENTION

This invention relates to wearable apparatus for providing facial muscular biofeedback.

Facial wrinkles can develop for a variety of reasons and are generally classified as either static or dynamic. Static wrinkles are the wrinkles and folds of the skin that are present when the face is at rest and the facial muscles are not acting on the skin so as to form a facial expression. Dynamic wrinkles are those that occur due to the effects of facial muscle activity on the overlying skin. With age, stress and environmental damage (such as sun exposure and smoking), dynamic wrinkles eventually become static wrinkles.

For many people, facial wrinkles are unwelcome and various treatments are available to reduce the appearance and/or development of wrinkles. For example, chemodenervation by means of a botulinum toxin injection can be used to reduce activity in certain facial muscle groups so as to prevent those muscles causing dynamic wrinkling of the skin that might lead to the development of static wrinkles. The most common site for a botulinum toxin injection is at the glabellar (frown) lines between the eyebrows. Other treatments suitable for the treatment of dynamic wrinkles include cosmetic surgery and dermal filler injections. All of these treatments are invasive, can involve some pain, and must be performed by a skilled practitioner.

Excessive activation of the facial muscles (e.g. due to habitual squinting or frowning) has also been found to be a factor in the occurrence of headaches and migraines. Recently, the use of botulinum toxin injections has been extended to treat headaches and migraine, with some studies finding complete or partial resolution in 75% of patients. Furthermore, significant numbers of patients received botulinum toxin injections for cosmetic indications report beneficial effects on headaches. Recent studies have also demonstrated that botulinum toxin injections into the frown area blocks frowning and elevates mood in depressed patients.

The facial muscles can themselves be affected by facial movement disorders such as hypertonia (increased muscle tone), synkinesis (abnormal and uncoordinated involuntary muscle activity) and hyperkinesia (exaggerated muscle activity). These disorders are frequently seen after facial nerve trauma and it is postulated that there is a "mis-wiring" of the nerves which results in inappropriate signals being sent to certain muscles (e.g. closing the eyes results in activation of smile muscles and vice versa). Hypertonia of glabellar and procerus muscles can also be seen in those who habitually squint or frown—for example, due to bright lights, photosensitivity, short-sightedness, use of computers/ smartphones, and psychological stress. This can lead to the development of significant facial wrinkles. Such activation of the glabellar and procerus muscles also pulls down the forehead and brow, eventually resulting in hooding of the upper eyelids.

As an alternative to a botulinum toxin injection, STX-Med produce a wearable device "Safetox" that inhibits the activation of the glabellar muscles through the application of an electric potential at the skin overlying the muscle. This can reduce dynamic wrinkles and hence prevent the development of static wrinkles but does not address the underlying cause of the wrinkles in a manner that permanently reduces wrinkling. Specifically, it is not designed to dynamically monitor muscle activity and mediate its effects in response to such activity.

The control of muscle activation can be improved through the use of biofeedback, which allows an individual to learn how to modify the activation of particular muscles by feeding back to the individual information representing measurements of the activation of those muscles. Biofeedback has been found to be useful in the treatment of various conditions such as Bell's Palsy and headaches. A review of general biofeedback practices is presented in "Evidence-based practice in biofeedback and neurofeedback" by C. Yucha & D. Montgomery, Association for Applied Psychophysiology and Biofeedback, 2008.

Devices suitable for enabling biofeedback include the MyoTrac Infiniti manufactured by Thought Technology Ltd. The MyoTrac device can provide an surface electromyographic (sEMG) signal captured from muscles to a computer, with the signal being used to control a video game or animation so as to provide feedback to the user—for example, with the activation of a leg muscle being used to control the ascent of a balloon in a video game. In this manner, the user can learn to improve their muscle control. However, MyoTrac is not suitable for use with facial muscles and does not allow a user to receive useful biofeedback indicative of complex facial expressions whilst engaged in normal everyday activities.

Headsets manufactured by NeuroSky and Emotiv Systems can be used to acquire electroencephalogram (EEG) signals that in practice can determine some aspects of facial movement, but those headsets do not provide any biofeedback to the user and are not therefore suitable for training a user how to improve their muscle control. Details of the NeuroSky and Emotiv Systems headsets can be found in US patent publications 2009/0214060 and 2007/0060830, respectively.

Various other publications deal have suggested using facial muscle activity for: controlling electronic devices, US 2012/0229248 and GB 2396421; monitoring drowsiness, US 2012/0229248 and WO 91/13584; for assessing the psychological state of a user, U.S. Pat. No. 6,102,847; and reducing neuromuscular tension, US 2011/0288445. None of these publications provide wearable apparatus for use whilst engaged in normal everyday activities that can provide biofeedback indicative of a wide range of facial expressions for the treatment of wrinkles and facial movement disorders.

There is therefore a need for improved apparatus for inhibiting or promoting the activity of facial muscles through biofeedback.

SUMMARY OF THE INVENTION

According to a first aspect of the present invention there is provided apparatus for providing muscular biofeedback, comprising:

facewear supporting biosensors arranged such that, in use, the biosensors are situated for detecting activity of a predetermined set of facial muscles;

a feedback unit for providing biofeedback to a wearer of the facewear; and a control unit coupled to the biosensors and the feedback unit and arranged to identify patterns in the signals from the biosensors characteristic of one or more predefined imbalances in muscle activity between the left and right sides of the face;

wherein the control unit is configured to, on identifying a pattern in the signals from biosensors characteristic of a first predefined imbalance in muscle activity between the left and right sides of the face, cause the feedback unit to provide biofeedback in correspondence with the imbalance.

Preferably the control unit is configured to identify a pattern in the signals from the biosensors characteristic of a first predefined imbalance in muscle activity between the left and right sides of the face by comparing the activity of predetermined corresponding facial muscles on the left and right sides of the face.

Preferably the control unit is configured to identify that the pattern in the signals from the biosensors is characteristic of the first predefined imbalance in muscle activity if the signals from the biosensors indicate that the asymmetry between the activity of the predetermined corresponding facial muscles on the left and right sides of the face exceeds a predetermined threshold for at least a predetermined minimum duration.

Suitably, if the duration and/or frequency of occurrence of periods of time when the control unit causes the feedback unit to provide biofeedback fall below a predetermined duration and/or predetermined frequency of occurrence, the control unit is configured to automatically decrease the predetermined threshold according to a stored scheme.

Preferably the minimum duration is $1/25^{th}$ of a second.

According to a second aspect of the present invention there is provided apparatus for providing muscular biofeedback, comprising:
facewear supporting biosensors arranged such that, in use, the biosensors are situated for detecting activity of a predetermined set of facial muscles;
a feedback unit for providing biofeedback to a wearer of the facewear; and
a control unit coupled to the biosensors and the feedback unit and arranged to identify patterns in the signals from the biosensors characteristic of one or more predefined facial expressions;
wherein the control unit is configured to, on identifying a pattern in the signals from the biosensors characteristic of a first predefined facial expression, cause the feedback unit to provide biofeedback indicative of the first predefined facial expression, the pattern in the signals from the set of biosensors characteristic of the first predefined facial expression being indicative of activation of a first subset of the predetermined set of facial muscles and indicative of a lack of activation of a second subset of the predetermined set of facial muscles.

Preferably muscles of the predetermined set are activated if their activity is above a respective threshold for at least a first minimum duration and are not activated if their activity is below a respective threshold for at least a second minimum duration.

Preferably the first and/or second predetermined minimum durations is at least $1/25^{th}$ of a second.

Suitably the respective thresholds are defined at the control unit in information defining the first predefined facial expression.

Suitably the pattern in the signals from the set of biosensors characteristic of the first predefined facial expression is further indicative of elongation of a third subset of the predetermined set of facial muscles, muscles of the third subset being antagonists of muscles of the first subset.

The biosensors supported at the facewear can include one or more of:
biosensors of a first type for measuring electrical activity of muscles of the predetermined set, the control unit being configured to infer the activity of muscles of the predetermined set from their electrical activity;
biosensors of a second type for measuring changes in the topography of skin overlying muscles of the predetermined set, the control unit being configured to infer the activity of muscles of the predetermined set from changes in the topography of the skin overlying the muscles; and
biosensors of a third type for measuring tensional forces of skin overlying muscles of the predetermined set, the control unit being configured to infer the activity of muscles of the predetermined set from tension in the skin overlying said muscles.

Suitably biosensors of the first type include any of sEMG sensors and electric potential sensors; biosensors of the second type include any of electric potential sensors, optoelectronic sensors, ultrasonic sensors, capacitive sensors, and photoelectric sensors; and biosensors of the third type include piezoresistive and/or piezoelectric sensors.

Suitably biosensors of the first and/or third type are supported at the facewear as adhesive patches for application to the skin overlying the respective muscles, in use the facewear being coupled to the biosensors of the third type by means of one or more electrodes presented at a non-adhesive face of the adhesive patches for engagement with corresponding electrodes of the facewear.

Preferably the biosensors include a proximity biosensor of a second type arranged on the facewear so as to, in use, be located approximately over a first muscle of the predetermined set but separated from the skin over that muscle by a distance of no more than a few millimeters, and the control unit being configured to infer the activity of the first muscle from changes in the signal from the biosensor due to changes in the proximity of the surface of the skin over the muscle due to contraction and relaxation of the muscle. The first muscle can be the temporalis, orbicularis oculi, frontalis, or glabellar muscles. The proximity biosensor can be an electric potential sensor, an ultrasound sensor or an optoelectronic sensor.

Preferably the control unit is configured to cause the feedback unit to indicate to the wearer that the facewear is not properly positioned when the proximity biosensor indicates that the distance to the skin over the muscle exceeds a predetermined distance.

Suitably the control unit is configured to switch between a low power mode and an operating mode in dependence on whether the signals from a plurality of the biosensors indicate that the facewear is being worn.

Suitably the biosensors include an optoelectronic sensor arranged on the facewear such that, in use, the sensor is directed for measuring changes in topology of skin overlying the zygomaticus muscle.

Preferably the control unit is further configured to process the pattern in the signals from the set of biosensors so as to identify the intensity of the first predefined facial expression from the magnitude of the activity of the facial muscles involved in the first predefined facial expression. Preferably the control unit is configured to cause the feedback unit to provide to the wearer an indication of the intensity of the first predefined facial expression.

Preferably the set of biosensors includes electric potential sensors arranged on the facewear so as to, in use, detect activity of the posterior auricular muscles.

Preferably the control unit is configured to infer the activity of a zygomaticus muscle from the activity of the posterior auricular muscle on the same side of the face.

Preferably the control unit is configured to infer the strength of activity of a zygomaticus muscle from the strength of activity of the posterior auricular muscle on the same side of the face.

Preferably the predefined facial expression involves smiling and the control unit is configured to determine the intensity of the smile from the strength of the activity of the posterior auricular muscles.

Suitably the feedback unit is configured to provide visual biofeedback to the user in the form of one or more of: constant or flashing light sources of fixed or varying colours, an optical head-mounted display, and eyeglass lenses of variable colour or transmittance. The intensity of the first predefined facial expression can be indicated by one or more of the colour, brightness, frequency of repetition and textual or graphical content of the visual biofeedback.

Preferably the facewear is eyewear and incorporates the feedback unit as one or more diffuse light sources located on or about lenses of the eyewear so as to, in use, illuminate the inner surface of the lenses directed towards the eyes of the wearer.

Suitably the feedback unit is configured to provide auditory biofeedback in the form of one or more of: constant or varying tones, beeps, recorded sounds, and computer-generated speech. The intensity of the first predefined facial expression can be indicated by one or more of the tone, amplitude and frequency of repetition of the auditory biofeedback.

Suitably the feedback unit comprises one or more earphones wearable in the ear of the user or a bone conduction audio device.

Suitably the feedback unit is configured to provide vibrational biofeedback and the intensity of the first predefined facial expression is indicated by the frequency or amplitude of the vibrational biofeedback.

Suitably the control unit is further configured to, on identifying a pattern in the signals from the set of biosensors characteristic of a second predefined facial expression, cause the feedback unit to provide biofeedback to the user indicative of the second predefined facial expression, the biofeedback provided in respect of the second predefined facial expression being distinguished from the biofeedback provided in respect of the first predefined facial expression.

Preferably the biofeedback provided in respect of the second predefined facial expression is distinguished from the biofeedback provided in respect of the first predefined facial expression by colour of visual biofeedback and/or frequency of audible/vibrational biofeedback.

Suitably the first predefined facial expression is characterised by an imbalance in muscle activity between the left and right sides of the face, and the control unit is configured to, on identifying the first predefined facial expression, cause the feedback unit to provide different biofeedback to each side of the face in correspondence with the asymmetry expressed by the first predefined facial expression.

Preferably the control unit is configured to store information defining which side of the face the first predefined facial expression is primarily associated with and to, in use, provide biofeedback at least primarily to that defined side of the face. Preferably the control unit is configured to, in use, provide biofeedback at least primarily and optionally only to the eye or ear of the wearer on the defined side of the face.

Suitably the facewear comprises eyewear and the feedback unit comprises corrective or non-corrective lenses arranged so as to in use be located over the eyes of the wearer, the lenses being configured to provide visual biofeedback by means of changes in the colour or transmittance of one or both of the lenses.

The apparatus preferably further comprises a data store defining parameters of one or more patterns in the signals from the biosensors characteristic of the first predefined facial expression.

Preferably the facewear is eyewear comprising a frame supporting a pair of lenses and two foldable arms for engagement about the ears or the sides of the head, the apparatus being activated on the arms being unfolded.

Preferably the facewear comprises eyewear having a frame supporting a pair of corrective or non-corrective lenses, a nosepiece for engagement with the bridge of the nose and a pair of supporting arms for engagement about the ears or with the side of the head, and the biosensors include one or more of:

at least one biosensor situated on a bridge of the frame approximately between the lenses and arranged for detecting the activity of one or more of the glabellar and frontalis muscles;

biosensors situated at or towards the distal ends of the supporting arms and arranged for detecting the activity of the anterior auricular and/or superior auricular and/or posterior auricular muscles;

biosensors situated on the supporting arms and arranged for detecting the activity of the temporalis and/or masseter muscles;

biosensors situated on the frame and arranged for detecting the activity of one or more of the orbicularis oculi and/or frontalis muscles;

at least one biosensor situated at the nosepiece arranged for detecting the activity of one or more of the glabellar and nasalis muscles; and biosensors situated on the frame and arranged for detecting the activity of one or more of the orbicularis oculi and/or frontalis muscles.

Preferably the biosensors are arranged such that, in use, any biosensors on the frame of the eyewear are not in contact with the skin overlying the respective muscles of the wearer and any biosensors on the arms, bridge and nosepiece of the eyewear are substantially in contact with the skin overlying the respective muscles of the wearer. Biosensors in contact with the skin can include one or more of sEMG sensors; electric potential sensors; piezoresistive sensors, and piezoelectric sensors. Biosensors not in contact with the skin can include one or more of electric potential sensors, optoelectronic sensors, ultrasonic sensors, capacitive sensors, and photoelectric sensors.

The first predefined facial expression can be one or more of frowning, squinting, disgust, smiling, clenching teeth, squeezing eyes shut, surprise, a hypertonic expression, a pathological synkinetic expression, a hem ifacial spasm, brow ptosis, and a hyperkinetic expression.

Suitably the facewear further comprises a passive movement sensor and the control unit is configured to cause the feedback unit to provide biofeedback only when a signal from the passive movement sensor indicates that the eyeglasses are being worn.

Preferably the control unit is operable in a calibration mode in which it is configured to store parameters defining the pattern in the signals from the biosensors characteristic of the first predefined facial expression.

Preferably a facial muscle is considered activated when the signal from its respective biosensor exceeds a predetermined threshold with respect to its calibrated maximum.

Suitably the first predefined facial expression is smiling and the control unit is configured to cause the feedback unit to provide biofeedback so as to enhance feelings of emotional wellbeing in the wearer.

Preferably the facewear comprises the feedback unit and control unit.

Preferably the control unit is configured to operate on the basis that the activity of the predetermined corresponding facial muscles is proportional to the level of the signals from their respective biosensors with respect to their calibrated maximums.

The feedback unit can be configured to provide biofeedback to the wearer by means of one or more of visual, auditory, vibrational or tactile indications.

Suitably the facewear comprises an audio headset having a frame for engagement about the ears and extending around the back of the head, the feedback unit comprising one or more earphones of the headset for providing audible biofeedback to the wearer, and the biosensors including one or more biosensors situated on the frame and arranged for detecting the activity of the anterior auricular and/or superior auricular and/or posterior auricular muscles and/or temporalis and/or masseter muscles.

Suitably the control unit is software for installation at a smartphone operable to wirelessly connect to the set of biosensors and the feedback unit.

According to a third aspect of the present invention there is provided apparatus for providing an indication of the emotional state of the wearer, comprising:
facewear supporting biosensors arranged such that, in use, the biosensors are situated for detecting activity of a predetermined set of facial muscles;
an indicator unit for providing an indication of emotional state; and
a control unit coupled to the biosensors and the indicator unit and arranged to identify patterns in the signals from the biosensors characteristic of one or more of a set of predefined facial expressions;
wherein the control unit is configured to, on identifying a pattern in the signals from the biosensors characteristic of a predefined facial expression of the set, cause the indicator unit to provide an indication of an emotional state corresponding to that predefined facial expression.

Preferably the indicator unit is configured to provide a visual indication of emotional state, with each emotional state being indicated by a different colour.

According to a fourth aspect of the present invention there is provided a method for calibrating apparatus as described herein, the method comprising:
entering a calibration mode of the control unit;
indicating to a wearer of the facewear to pull a predetermined sequence of facial expressions;
in response to each facial expression of the sequence, storing at the control unit parameters defining a pattern in the signals from the biosensors characteristic of the respective facial expression; and
processing the stored parameters so as to generate calibration information for each of the biosensors defining a correspondence between the signal from that biosensor and the activity of the respective facial muscle.

Preferably the predetermined sequence of facial expressions includes a neutral facial expression.

Preferably the pattern in the signals from the biosensors characteristic of the first predefined facial expression is determined from stored information defining the expected activation of muscles for the first predefined facial expression and the calibration information for at least some of the biosensors.

Preferably the stored information defining the expected activation of muscles for the first predefined facial expression defines each muscle as activated or not activated.

Suitably the first predefined facial expression is selectable at the control unit from a list of predefined facial expressions, each having associated stored information defining the expected activation of muscles for that predefined facial expression.

According to a fifth aspect of the present invention there is provided a method for the treatment of brow ptosis comprising:
injecting botulinum toxin into at least one of the glabellar and orbicularis oculi muscles; and
directing a patient to use apparatus configured in accordance with the second aspect of the present invention in which the biosensors include biosensors for detecting the activity of at least one of the glabellar and orbicularis oculi muscles, and the first predefined facial expression includes brow ptosis.

DESCRIPTION OF THE DRAWINGS

The present invention will now be described by way of example with reference to the accompanying drawings, in which.

DETAILED DESCRIPTION OF THE DRAWINGS

The following description is presented to enable any person skilled in the art to make and use the invention, and is provided in the context of a particular application. Various modifications to the disclosed embodiments will be readily apparent to those skilled in the art.

The general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Biofeedback is a well-established method for improving muscle control and is often used as part of neuromuscular retraining following neurological conditions such as stroke. The inventor of the present invention recognises that biofeedback is particularly useful for facial treatments because the facial muscles used for expression are generally lacking the muscle spindles that provide sensory feedback to the brain about the degree of stretch of tension across a muscle. The present invention provides wearable apparatus that can be conveniently used by a user for long periods of time with the aim of training the user to minimise the development of facial wrinkles through improvement of their facial expressions, or with the aim of addressing neurological or muscular conditions that affect proper control of the facial muscles. The present inventions teaches the use of an advantageous selection of facial muscles for the efficient improvement of facial expression without requiring the use of multiple unsightly wired sensors. A further aspect of the present invention provides wearable apparatus that can be worn by a user so as to indicate the emotional state of that user to his/herself or to others.

Figure 1:
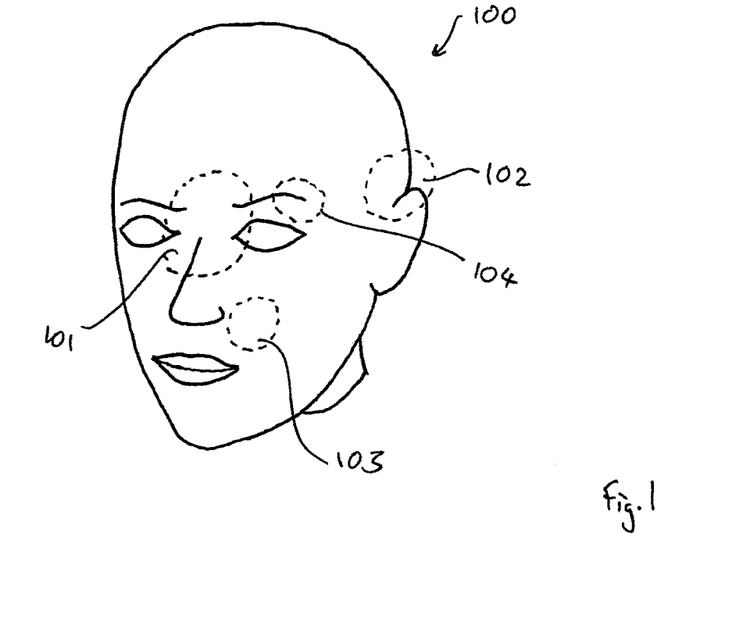
FIG. 1 is an illustration of the locations of various facial muscle groups.

FIG. 1 illustrates the location of several key facial muscle groups that have been identified as having a significant role in causing facial wrinkles. The location of the muscle groups is shown on human head 100. Group 101 comprises the procerus, corrugator supercilii, depressor supercilii and nasalis muscles, which are activated when stressed, frowning, or exhibiting disgust and can cause wrinkles around the eyes, forehead and upper nasal region. The procerus, corrugator supercilii and depressor supercilii can be referred to as the glabellar muscles. Group 102 comprises the anterior auricular, superior auricular and posterior auricular muscles, which are activated during smiling and are therefore generally associated with positive expressions. Where eyebrow elevation due to frontalis muscle activity causes activation of these peri-auricular muscles, such as during the expression of surprise, the sensing of forehead or cheek movement to distinguish between the expressions may be required. The levator labii, alaeque nasi and zygomaticus major and minor muscles of group 103 are the main muscles involved in smiling together with risorius and depressor labii inferioris. Group 104 comprises the orbicularis oculi, which is used to close the eye.

The glabellar region of the face describes the region overlying the procerus muscle (depressor of the forehead and cause of the horizontal wrinkle between the eyes on frowning) and the corrugator supercilii muscles which has transverse and oblique components that together depress and medialise the brow. A smaller muscle, the depressor supercilii, is closely related to the corrugators and outer fibres of the orbicularis oculi muscles that encircle the eye. This also acts as a medial brow depressor. Anatomical dissections have demonstrated that the nerve supply to these muscle and well as the nasalis muscle, which wrinkles the nasal sidewall, are innervated by a branch of the zygomatic division of the facial nerve. The act of frowning typically leads to activation of all of these muscles in a synkinetic fashion, a fact that can be exploited to provide biofeedback.

A summary of the facial muscles active for a range of facial expressions is shown in table 1. In the table, the symbol "< >" indicates that gross movement of the skin overlying the respective muscle can be characterised as stretching, and the symbol "> <" indicates that gross movement of the skin overlying the respective muscle can be characterised as creasing. It is possible to detect both types of gross movement with a MEMS sensor, a piezoelectric or piezoresistive sensor, and optical sensors, and creasing of the skin may be detected at apparatus worn on the face of a user by a proximity sensor (such as an ultrasonic, capacitive or photoelectric sensor) because the creasing of the skin causes it to protrude from the plane in which it normally lies. Direct detection of the electrical activity of the muscles can of course be performed in the manner discussed herein through the use of sEMG or electric potential sensors.

TABLE 1

|  | Frown | Squint | Disgust | Smile | Clench teeth | Squeeze eyes shut | Surprise |
| --- | --- | --- | --- | --- | --- | --- | --- |
| Corrugator supercilii | >< | >< | >< |  |  | >< | <> |
| Depressor supercilii | >< | >< | >< |  |  | >< | <> |
| Procerus | >< | >< | >< |  |  | >< | <> |
| Orbicularis oculi (pars lateralis) |  | >< |  | >< |  | >< | <> |
| Orbicularis oculi (pars medialis) |  |  |  |  |  | >< | <> |
| Nasalis | >< |  | >< |  |  | >< |  |
| Temporalis and masseter |  |  |  |  | >< |  |  |
| Frontalis |  |  |  |  |  |  | >< |
| Posterior auricular |  |  |  | >< |  |  | <> |
| Zygomaticus |  |  |  | >< |  |  |  |
| Levator labii |  |  |  | >< |  |  |  |

According to the present invention, biofeedback apparatus is provided as facewear, such as eyewear (e.g. in the style of glasses, sunglasses, protective eye shields etc.) or a headset (e.g. an audio headset comprising a pair of earphones for listening to music or making telephone calls). Facewear can include any wearable devices that in use at least partly overlie the facial muscles of the wearer.

Figure 2:
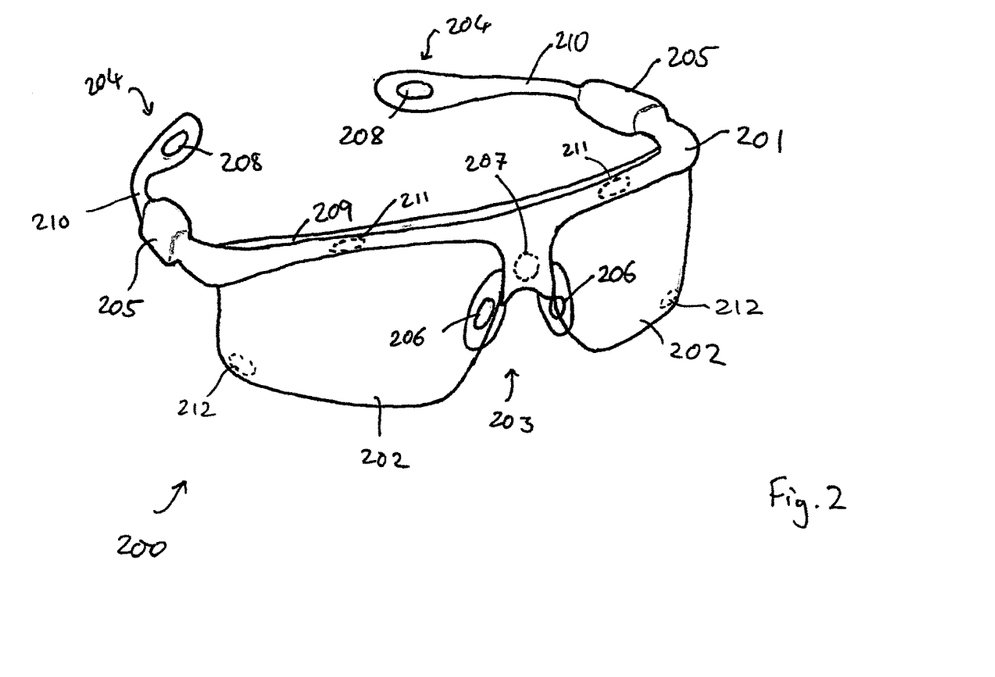
FIG. 2 is a schematic diagram of eyewear configured in accordance with the present invention.

In a first example of the present invention shown in FIG. 2, the facewear is provided as eyewear, in this case a pair of eyeglasses. Eyewear 200 comprise a frame 201 supporting a pair of lenses 202 in any suitable configuration. The eyeglasses include two arms 210 extending from the frame to the earpieces 204 which are configured to hold the glasses in place at or around the ears of a user. The arms could form a single piece with the frame, or the arms could be foldable into the frame so as to allow the glasses to be stored more compactly. The glasses also comprise a nosepiece or nosepieces 203 so as to allow the glasses to sit comfortably at the nose of the user. The lenses 202 could be made of any suitable material, including glass and plastic (such as polycarbonate) and could comprise filters or light sources for modifying the vision of the user when wearing the glasses. The lenses could be any kind of corrective lens (e.g. for short or long sight, or a combination thereof) but need not be corrective and could be "false" lenses or the lenses of sunglasses. Such lenses could incorporate a display screen.

The glasses 200 include a set of biosensors for detecting the activity of facial muscles of a user. By arranging the biosensors at particular points on the glasses, the activity of different facial muscles can be detected. For example, biosensors 206 and/or 207 could be provided at nosepiece(s) 203 such that, when the glasses are worn, the biosensors engage with one or more of the glabellar muscles (preferably by means of biosensor 207) and nasalis muscles (preferably by means of biosensors 206). Biosensors 208 could be provided at the earpieces 204 such that, when the glasses are worn, the biosensors engage with one or more of the anterior auricular, superior auricular and posterior auricular muscles. Biosensors 211 could be provided at frame 201 to allow the activity of the orbicularis oculi muscles to be detected. Optical or other kinds of biosensors arranged for detecting changes in the topology of the zygomaticus or levator labii muscle can be provided at positions 212. There could be more than one biosensor at each of the exemplary locations shown in FIG. 2.

The eyeglasses shown in FIG. 2 are merely schematic and it is to be understood that the shape, style, size and fit of the glasses may vary so as to allow the biosensors to engage with the facial muscles of a given user in the manner described herein. Preferably the eyeglasses would be fitted by a healthcare professional or optician so as to ensure optimal engagement of the biosensors with the muscles of the user.

The biosensors could be any kind of biosensors for detecting the activity of facial muscles by any mechanism, including electrical, topographical, neurological, and mechanical transduction sensing mechanisms. Different types of biosensor could be used at different locations on the glasses.

Preferably the biosensors detect the electrical activity of muscles. Suitable sensor types include surface electromyographic (sEMG) sensors (e.g. contact sensors manufactured by mc10 or Toumaz) and electric potential (EP) sensors (e.g. a Plessey EPIC sensor). Most preferably the sensors are electric potential sensors because these exhibit high sensitivity and do not require a conductive medium such as a gel or conductive adhesive patch to electrically couple the sensor to the skin.

Biosensors for detecting the movement of the skin overlying muscles could be optical, ultrasound or photoelectric sensor configured so as to measure changes in the topology of the skin overlying a given muscle—i.e. as a muscle contracts it generally creates a bulge underneath the skin, pushing the surface of the skin upwards towards an overlying sensor. For example, biosensors 207 and 211 could be optoelectronic sensors configured to determine the activity of the respective facial muscles by directing LED or laser light at the skin overlying those muscles and determining the activity of those muscles from the changes in the topography of the skin indicated by the LED or laser light reflected from that area of skin (i.e. in much the same way as an optical computer mouse determines movement over a surface). Ultrasound sensors can be configured to measure the proximity of a skin surface to which they are directed through time of flight measurements.

Electric potential (EP) sensors can also be used to detect the proximity of the surface of the skin. An EP sensor spaced apart from the skin by a few millimeters can detect changes in the proximity of skin overlying a muscle as the muscle contracts due to resulting changes in the electrical environment of the sensor. It is envisaged that the same EP sensors of the facewear could be used in two modes, depending on whether the EP sensor is in contact with the skin: in a first electrical mode when an EP sensor is in contact with the skin, and a second proximity mode when an EP sensor is not in contact with the skin. This can allow glasses that are not custom fitted to a person to be used by people with a wide range of head shapes and sizes.

Biosensors for detecting tension in the skin overlying muscles could be a piezoresistive or piezoelectric sensors (such as a flexible membrane comprising a piezoresistive or piezoelectric organic molecular metal). This type of sensors operates by measuring the stretching and creasing of the skin overlying a muscle as the muscle contracts and relaxes. Such sensors would preferably be incorporated in adhesive patches for application to the skin over the target muscles. The sensors could be microelectromechanical (MEMS) sensors (e.g. configured as a strain gauge). The biofeedback actuator can be mounted directly to the adhesive patch to provide direct feedback when muscle activity passes a threshold.

Electroencephalographic (EEG) sensors can also be used to pick up the EMG indicative of muscle activity.

Different biosensors could be different types of biosensor that employ different sensing mechanisms. For example, nosepiece biosensors 206 and earpiece biosensors 208 are preferably electric potential sensors since those sensors can be arranged to sit in contact with the skin overlying the facial muscles of interest. Biosensors that it are difficult to bring into firm contact with the skin are preferably instead optoelectronic sensors or proximity sensors. Since EP sensors can be used as both contact and non-contact sensors, all the facewear sensors could be EP sensors.

In the case that sEMG sensors are used to detect the electrical activity of muscles, it can be advantageous to apply conductive patches or gel to the skin of the user at the locations at which the biosensors will lie when the glasses are worn by the user. This can help to improve the quality of the signal acquired by the biosensors. Preferably however, electric potential sensors are used in preference to sEMG sensors since they offer high sensitivity without requiring the use of conductive gels or patches needed by sEMG sensors to electrically couple the sensor to the skin.

In less preferred embodiments, at least part of the biosensors themselves (e.g. sEMG or piezoresistive sensors) could be incorporated within a flexible membrane that is applied to the skin over a target muscle, with the membrane presenting electrical contacts to the glasses for engagement with corresponding contacts on the glasses. In this manner, the glasses and the flexible membranes are in combination wearable apparatus comprising biosensors for detecting the activity of facial muscles.

The glasses 200 further include a feedback unit by means of which biofeedback can be provided to the user. The feedback unit could comprise one or more components for delivering one or more of visual, auditory, vibrational or tactile feedback to the user. For example, in FIG. 2 a light source 209 in the form of a strip operable to emit diffuse light of various colours is provided. Facewear of the present invention could alternatively or additionally include one or more earphones for providing auditory feedback to the user, or vibrational devices for providing vibrational feedback. Earphones could be provided separately to the glasses. In less preferred embodiments the feedback unit is provided separately to the facewear.

A control unit 205 is provided to receive signals from the biosensors and in response cause the feedback unit to provide indications to the user by way of biofeedback. As shown in FIG. 2, the control unit is preferably part of the facewear, but in less preferred embodiments the control unit is provided separately—for example, the control unit could be embodied in software at a smartphone or watch, operable to wirelessly couple to the biosensors and feedback unit.

According to a first embodiment of the present invention, the control unit is configured to detect facial expressions of the user/wearer and in response provide appropriate biofeedback to the user/wearer. This is achieved by arranging that the control unit monitor the signals from the biosensors so as to identify patterns characteristic of one or more predefined facial expressions. Since each facial expression is achieved through the activation of a particular set of facial muscles, by monitoring the signals from biosensors monitoring the muscles involved in a facial expression, that facial expression can be identified. In this manner, the user can receive useful biofeedback indicating facial expressions that might lead to, for example, wrinkling or headaches/migraines. The user can utilise the biofeedback in order to help with, for example, avoiding squinting, or other disadvantageous facial expressions.

As set out in table 1, it is generally sufficient to determine in a binary fashion which muscles are activated. In other words, a facial expression can be characterised by a particular set of facial muscles exhibiting activity above a predetermined threshold for at least a predetermined minimum period of time. The activity of a facial muscle can be inferred from the level of the signal from its respective biosensor. For example, if the activity threshold for a muscle is 60% and the minimum period is $\frac{1}{25}^{th}$ second then the muscle is considered to be activated when the signal from the biosensor for that muscle exceeds 60% of its calibrated maximum for at least $\frac{1}{25}^{th}$ second. It follows that the intensity of the facial expression can be inferred from the signal level of the muscles active in making the facial expression.

The facial expressions are defined as expected patterns in the activity of facial muscles that can be identified by the apparatus through monitoring the signals from the biosensors provided for those muscles.

Information defining the expected pattern of signals corresponding to a facial expression in respect of which the apparatus is to provide biofeedback is stored at the control unit. For example, the control unit could store information defining for a given facial expression a set of facial muscles that are activated along with their respective activity thresholds. The thresholds for each of the muscles could be the same. It is advantageous if the information further defines for the target facial expression muscles that are to be not activated in order for the facial expression to be considered to have been made. A muscle can be considered not activated if its activity is below a respective threshold for a minimum period. This improves the accuracy of the facewear apparatus.

For facewear that makes use of sensors operable to detect the antagonistic relaxation of muscles, it is further advantageous to use those sensors to further improve the accuracy of expression detection. This allows a third category of muscle activity to be defined at the control unit for a facial expression: as well as "activated" and "not activated", we can add "antagonist"—i.e. those muscles that relax and become elongated due to the activated muscles acting in opposition to them. Suitable sensors include those configured to detect tension in the skin overlying a muscle and those configured to detect changes in topography of the skin overlying a muscle due to its contraction and relaxation.

For example the glabellar muscles and orbicularis oculi pars lateralis muscles are antagonistic to the frontalis muscles for the expression of surprise which lifts the brows and stretches the glabellar muscles, and to a lesser extent the muscles underlying the "crows feet" region.

Biosensors for detecting changes in topography of the skin would typically be mounted on the facewear such that, when worn, the sensors are spaced no more than a few millimeters from the surface of the skin overlying the target muscles. It can be advantageous to use such proximity biosensors on eyeglasses for the detection of activity in muscles not readily contactable by sensors mounted on the frame of the glasses, for example the temporalis, orbicularis oculi, frontalis or glabellar muscles.

Proximity biosensors can be used to determine when the facewear is not properly positioned. This can be achieved by arranging that the control unit causes the feedback unit to indicate to the wearer when one or more proximity biosensors indicate that the distance from those sensors to the surface of the wearer's skin exceeds a predetermined distance. Proximity biosensors mounted on the frame of eyewear for detecting the activity of orbicularis oculi, frontalis or glabellar muscles (e.g. at 211) are particularly useful for determining whether the eyewear is optimally positioned in-situ on the wearer's face. Such sensors can detect, for example, when the glasses slip down the nose of the wearer. The use of sensors on each side of the facewear can be used to determine whether facewear is mounted straight on the wearer's face by monitoring that the distances from the sensors to the surface of the skin are equivalent—if not, the control unit can infer that the facewear is not mounted symmetrically on the user's face. This is particularly important if the facewear is used to monitor left/right imbalances in the facial muscles. In some embodiments, the facewear could comprise one or more proximity sensors dedicated for detecting whether the glasses are properly mounted on the wearer's face, those sensors not being biosensors for measuring the activity of facial muscles.

In preferred embodiments of the present invention, the control unit is configured to determine when the facewear is mounted on the face by monitoring when the output from at least one and preferably all of the biosensors exhibit the changes characteristic of the change in electrical environment of those sensors. This is particularly advantageous when at least some of the biosensors of the facewear (and those monitored) are EP sensors. The control unit could be configured to transition from a low power standby mode to an operating mode on the control unit determining that the facewear is mounted on the wearer's face.

Previous devices for measuring the activity of the muscles of the face have typically used the zygomaticus muscle to detect smiling. However, the activity of this muscle is difficult to detect using eyeglasses because no part of the eyeglasses overlies the zygomaticus muscle. The orbicularis oculi muscles can be used but they lack sensitivity as a measure of the degree to which the user is smiling. The inventors have found however that the posterior auricular muscle can not only be used to detect smiling in a user but that the magnitude of its activation is proportional to the intensity of the smile. More specifically, the magnitude of the activation of a particular posterior auricular muscle is proportional to the magnitude of the activation of the zygomaticus muscle on the same side of the face. The control unit of the present invention is therefore preferably configured to make use of the posterior auricular muscle in place of the zygomaticus in algorithms for detecting patterns indicative of smiling in the output of the biosensors of the eyeglasses. Activation of the posterior auricular muscle can be detected by biosensors located at the earpieces of the eyeglasses so as to in use overlie the posterior auricular muscle, preferably electric potential sensors.

Following idiopathic facial palsy (known also as Bell's palsy) the first extra-cranial muscles to be re-innervated by the recovering facial nerve are the peri-auricular muscles. Application of a sensor over the posterior auricular muscle therefore provides a discrete and early monitoring method for detecting the initial stages of nerve recovery.

The facial expressions detected by apparatus of the present invention could be frowning, squinting, disgust, smiling, clenching teeth, squeezing eyes shut, surprise, as well as expressions peculiar to the medical condition of a user, such as a hypertonic expression, a synkinetic expression, a hemi-facial spasm, brow ptosis, and a hyperkinetic expression. For facial expressions detected by the present invention that are characterised by an imbalance in muscle activity between the left and right sides of the face, it can be advantageous for the control unit to cause the feedback unit to provide asymmetric biofeedback to the wearer: i.e. to provide different biofeedback to each side of the face in correspondence with the asymmetry expressed by the facial expression. Most preferably, when the pattern characteristic of a facial expression is defined at the control unit, the side of the face with which the asymmetry is primarily associated is also defined, and the control unit is configured to cause the feedback unit to provide biofeedback at least primarily to that side of the face. For example, for a user suffering from hyperkinesia primarily affecting one side of the face, the apparatus is configured to provide biofeedback primarily to the eye or ear on that side of the face so as to inform the user when that hyperkinetic facial expression as defined by patterns stored at the control unit is made.

By suitably defining more than one pattern at the control unit for the control unit to detect, the facewear apparatus could be configured to provide different biofeedback to the wearer when different facial expressions are detected. The biofeedback could be distinguished by, for example, the colour of visual biofeedback, or the tone of audible biofeedback. For example, if multiple facial muscle activation patterns are simultaneously detected by the control unit, it could cause the feedback unit to emit both colours so as to cause the user to perceive a blend of both colours. In this manner, the brain can efficiently comprehend the facial muscle activations that it cannot itself directly quantify.

The excessive activation of the glabellar and often orbicularis oculi can also lead to hooding of the upper eyelids due to brow ptosis. Treatment of brow ptosis conventionally involves injection of botulinum toxin into the brow depressor muscles, or surgery. The inventor has identified that it is surprisingly effective in the treatment of brow ptosis for patients to make use of the facewear apparatus of the present invention following the injection of botulinum toxin into the brow depressor muscles, particularly in the period in which the botulinum toxin wears off (typically 3-5 months post injection). Facewear apparatus used in this method includes biosensors for the monitoring of at least some of the brow depressor muscles, with the control unit of the apparatus being configured to identify one or more facial expressions indicative of brow ptosis.

According to a second embodiment of the present invention, the control unit is configured to identify patterns in the signals received from biosensors of the facewear characteristic of imbalances in the muscle activity between the left and right sides of the face. The imbalances are defined as expected patterns in the activity of facial muscles that can be identified by the apparatus through monitoring the signals from the biosensors provided for those muscles. Thus, the facewear can indicate to the user when there is an imbalance in the activation of pairs of equivalent muscles from the left and right sides of the user's face. This can be useful, for example, for the treatment of Bell's Palsy patients often experience "drooping" on one side of the face and cannot properly activate muscles on that affected side.

Information defining the expected pattern of signals corresponding to an imbalance in respect of which the apparatus is to provide biofeedback is stored at the control unit. In response to the control unit identifying a predefined imbalance, the control unit causes the feedback unit to provide biofeedback to the user in correspondence with the imbalance. Preferably this is by providing different biofeedback to each side of the face in accordance with the asymmetry inherent in the expression, but in less preferred embodiments this could be by providing biofeedback in any manner to the user.

The control unit is configured to compare the activity of corresponding facial muscles on the left and right sides of the face. This is achieved by comparing the signals from the respective biosensors for those facial muscles. For example, if the imbalance defined at the control unit is an imbalance in facial muscles involved in smiling, the control unit could be configured to determine when the activity of the posterior auricular muscle (used in place of the conventional zygomaticus) on one side of the face exceeds the activity of the posterior auricular muscle on the other side of the face to a predetermined degree for a predetermined period (e.g. the signals from those muscles is indicative of an imbalance of activity above a threshold of 150% for at least $\frac{1}{25}^{th}$ second).

In the same manner described above in relation to the first embodiment, information defining the expected pattern of signals corresponding to a target muscular imbalance in respect of which the apparatus is to provide biofeedback is stored at the control unit. For example, the control unit could store information defining for a given imbalance the activity asymmetry threshold for a set of facial muscles. The thresholds for each of the muscles could be the same. It can be advantageous if the information further defines for the target facial expression muscles that are to be not activated in order for the facial expression to be considered to have been made. A muscle can be considered not activated if its activity is below a respective threshold for a minimum period. This can improve the accuracy of the facewear apparatus in only providing biofeedback when a particular facial expression is being made.

It is envisaged that the first and second embodiments described herein can be used together such that the facewear is configured to only provide biofeedback indicating a predefined imbalance in muscular activity when that activity relates to a predefined facial expression.

In the case that the facewear is being used to treat hypertonia, it can be advantageous for the control unit to automatically reduce the threshold asymmetry above which biofeedback is provided as the condition improves. This can be achieved by monitoring the duration and/or frequency of occurrence of biofeedback provided by the apparatus. If the duration and/or frequency of occurrence of biofeedback falls by a predetermined amount or proportion, or if the duration and/or frequency of occurrence of biofeedback falls below a predetermined duration/frequency, the control unit can be configured to automatically decrease the predetermined threshold in accordance with a defined scheme. For example, if the asymmetry threshold for the level of activity in the orbicularis oculi muscles on the left and right sides of the face is initially 150%, this is automatically reduced to a threshold of 140% on the duration of activation falling below 5% of the time the user is performing rehabilitation exercises with the device due to improvement of muscular control through use of the device.

The control unit controls the indications provided by the feedback unit by means of control signals, which could be expressed, for example, as a simple analogue or multi-level voltage, or digital data. The control unit could be configured to generate control signals that cause the feedback unit to indicate in a binary sense whether or not the target facial expression or muscle imbalance is detected. Alternatively, the control unit could be configured to indicate the level or degree of the target facial expression or muscle imbalance in an analogue or multi-level fashion. For example, the intensity of a target facial expression could be expressed by intensity of colour (either in terms of brightness or saturation) emitted by light source 209.

It has also been found that the physical act of smiling has a positive effect on emotion. Since apparatus configured in accordance with the present invention can provide biofeedback to the user indicating when they are smiling, the apparatus can be used to improve the mood of the user by promoting the action of smiling. Certain medical conditions are associated with a reduction in the frequency or magnitude of smiling and this apparatus can be used to assess the severity of these conditions. A common example is the "mask-like" facial expression in Parkinson's disease, and the anhedonia of depression. Similarly, as the present invention can provide biofeedback to the user when they are frowning, the apparatus can be used to monitor negative emotions.

In addition to addressing conditions that result from improper activation of facial muscles, apparatus configured in accordance with the present invention can also be used to help patients to recover from conditions affecting the facial muscles of the face, such as Bell's Palsy, synkinesis, and hyperkinesia, amongst others.

In order to avoid the user receiving biofeedback for minor muscle activations (which could be involuntary or not indicative of any particular facial expression), the control unit is preferably configured to only provide biofeedback if the detected muscular activity exceeds a predetermined threshold for a predetermined minimum length of time. It has been found that $1/25^{th}$ second represents a reasonable cut-off for distinguishing between fleeting expressions or noise, and genuine facial expressions of the kind the apparatus of the present invention is designed to detect. Other threshold values could be used, such as $1/30^{th}$, $1/20^{th}$, $1/15^{th}$ or $1/10^{th}$ second.

In the example shown in FIG. 2, the lenses 202 could form part of the feedback unit in that they provide a heads-up display for indicating textually or graphically the facial muscle activations detected by the biosensors. In a particularly preferred embodiment, the transmittance or colour of lenses 202 could be controlled by the control signals from the control unit so as to provide biofeedback to the user. This is a particularly effective mechanism to teach the user to avoid certain facial expressions. For example, if the control unit determines that the user is squinting or exhibiting some other stress response, the control unit can cause the lenses to become at least semi-opaque or change colour. It can be advantageous to arrange that the lenses are most transparent only when no significant activity is detected at the facial muscles monitored by the biosensors. To give another example, if the control unit determines that a facial muscle activation pattern exhibits an imbalance between the left and right sides of the face, the lens on the side that is least activated could become semi-opaque, or vice versa.

In order to offer adjustable transmittance, each lens could include a pair of polarized filters, one or both having a polarization that can be controlled by means of the control signals from the control unit. As is known in the art, by adjusting the plane of polarization of one or both of the filters, the transmittance of the lens can be controlled.

In the example shown in FIG. 2, the arms 210 of the glasses are preferably foldable and the apparatus is configured to become enabled for use (e.g. power up) on the arms being unfolded into positions in which the eyeglasses can be worn by the user. This can be achieved through the use of switches at the hinges (not shown) between the frame 201 and arms 210, and can help to conserve battery power at the device.

The control unit and feedback unit need not be located at the facewear. For example, the feedback unit could be provided as one or more earphones for engagement in or around the ear(s) of the user and arranged to provide audible feedback. The control unit could be provided at a data processing device coupled by wire or wirelessly to the biosensors and/or feedback unit. For example, the control unit could be embodied in software arranged to execute at a smartphone or other portable data processing device (e.g. a tablet computer or media player). The control unit software could be coupled to the biosensors by means of a wireless connection provided by the smartphone (e.g. a Bluetooth 4.0 low energy connection), with the facewear being provided with an appropriate transceiver to support such a wireless connection.

The feedback unit is preferably integral with the facewear and in the case that the control unit is supported at a smartphone or watch, the feedback unit could also be configured to communicate over a wireless connection to the smartphone. Alternatively the feedback unit could be provided at the smartphone or watch—for example, the vibrational mode of a smartphone or watch could be employed to provide discrete vibrational biofeedback to the user, and/or the screen could be used to provide visual biofeedback, and/or one or more earphones/headphones/an audio headset coupled to the phone could be used to provide audible biofeedback.

The degree of activation of a muscle pattern can be indicated using vibrational feedback by the frequency or amplitude of the vibrational source.

As discussed herein, it can be advantageous for the facewear to provide biofeedback indicating the intensity of a facial expression or degree of imbalance in a set of one or more facial muscles. This is an alternative to providing a binary indication (i.e. whether or not a facial expression is being made/that there is at least a certain level of asymmetry). The intensity of a facial expression or degree of imbalance could be indicated by, for example, the tone, amplitude or frequency of repetition of sound emitted by a feedback unit, the frequency, amplitude or frequency of repetition of vibrations from a vibrational source, or the colour, intensity, or textual or graphical information content of visual biofeedback. For instance, a louder sound or higher pitched tone could be used to indicate greater muscle activation. Audible feedback could also be provided by means of recorded sounds (such as pre-recorded speech), computer-generated speech, constant or varying tones, music and beeps.

Tactile feedback could be provided by the feedback unit (or a component thereof) as an item of clothing configured to adapt its configuration in response to the control signals from the control unit. For example, the item of clothing could be a hat or gloves operable to constrict about a body part at which it is worn in response to appropriate signals from the control unit to provide biofeedback.

The control unit could be configured to record representations of the signals received from the biosensors for subsequent transmission over a wired or wireless connection. This can allow the progress of a user or patient to be monitored.

It is envisaged that wearable apparatus configured in accordance with the present invention, such as glasses or a headset, can be used in a passive mode to promote certain facial muscular activities and inhibit others.

In order to allow the control unit to accurately infer the activity of facial muscles from the signals received from biosensors of the facewear, it is generally necessary to calibrate the apparatus. This is most advantageously achieved by causing the wearer to pull a predetermined sequence of facial expressions whilst the apparatus is in a calibration mode. The facial expressions are chosen so as to, when performed in sequence, cause each of the facial muscles targeted by the sensors of the facewear to exhibit substantially their full range of activation, from relaxed to fully activated. In its calibration mode, the control unit records the range of signals that correspond to the range of muscle activities triggered by the performing of the facial expressions by the user. The calibration process could be performed with the aid of a computer configured to display to a user the facial expression to be performed and to inform the control unit which facial expression is being performed so that the control unit can correlate the signals it detects to the activity of the muscles as a result of that facial expression. The sequence of facial expressions preferably includes a neutral expression in order to define a baseline relaxed state for the muscles of the face. For users with hypertonic conditions, a medical professional would typically be involved in setting an appropriate signal level for biosensors arranged to detect hypertonic muscles such that the baseline signal for those muscles more closely reflects the expected normal tonic condition of the muscles.

However, it is further advantageous if the control unit is operable to provide a training mode in which the control unit first causes the feedback unit to indicate to the user that they are to make one of a predetermined set of facial expressions, the control unit subsequently or simultaneously indicating to the user the degree of correlation between the signals received from the biosensors and a stored representation of signals that would be expected from the biosensors for that facial expression. The set of facial expressions could include smiling, frowning, squinting and raising of the eyebrows, in addition to their inverse counterparts (e.g. not smiling, not frowning, not squinting, not raising eyebrows). Preferably the facial expression would be selectable by a user or medical professional through one or more user inputs provided at the apparatus (e.g. buttons, dials, switches, touch-screen inputs), or through appropriate wired or wireless communication between the control unit and another data processing system, such as a laptop.

At least part of a biosensor could be provided as a membrane for connection to the facewear and engagement with a set of electrodes of the facewear so as to allow signals from the sensor to be received at the control unit. This allows the biosensors, or those parts in contact with the skin, to be readily replaced.

Figure 3:
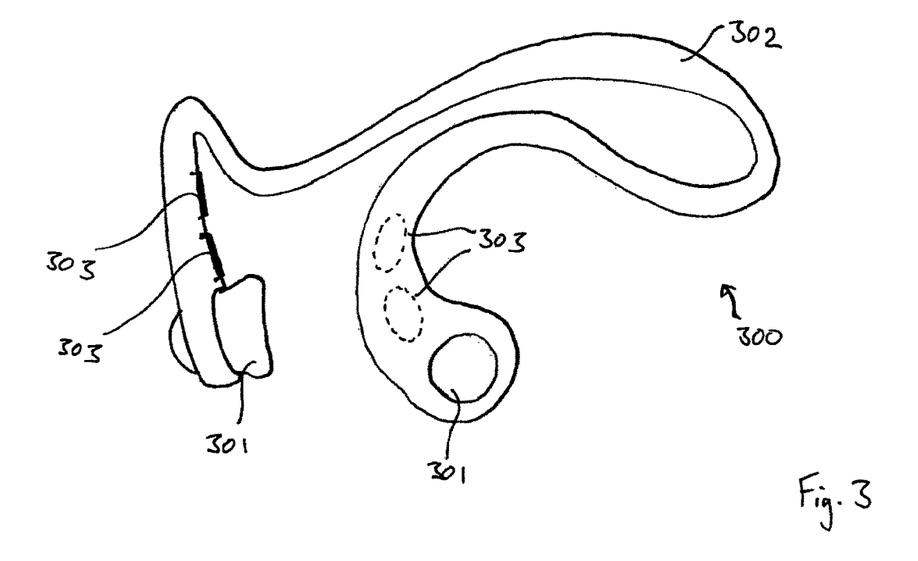
FIG. 3 is a schematic diagram of a headset configured in accordance with of the present invention.

Another embodiment of the present invention is illustrated in FIG. 3 in which the facwear is an audio headset 300 comprising a pair of earphones 301 as the feedback unit. The headset includes biosensors 303 for detecting activity of the auricular muscles. The earphones are connected by a band 302 which is preferably a resilient flexible connection between the earphones and configured such that, when worn by a user, the band sits about the rear of the skull so as to bring biosensors 303 into contact with the skin of the user over, for example, the auricular muscles. In less preferred variations of the second embodiment, the band need not be present and the biosensors would be supported at parts of the earphones themselves configured to engage with the skin over the auricular muscles. The biosensors 303 could be of any of the types discussed above in relation to other forms of facewear.

It can be advantageous to provide as part of the wearable apparatus one or more additional biosensors as adhesive patches for application to the skin over facial muscles that cannot be straightforwardly engaged by biosensors supported at a pair of glasses or headphones/an audio headset. Additional biosensors provided as adhesive patches could be connected into the control unit at appropriate connectors by thin wires. Such biosensors would, for example, allow the control unit to receive signals from the levator labii and/or zygomaticus muscles of the cheek. This enables the biofeedback apparatus to operate with a wider range of facial muscular activity.

According to a further aspect of the present invention, wearable apparatus as described herein is configured to additionally or alternatively provide an indication of the emotional state of the user to other persons. Since the set of biosensors (some or all of 206/207/208/211) detects the activation of various facial muscles, the control unit can determine the facial expression made (or attempted) by the wearer of the glasses. The control unit can therefore be configured to cause feedback unit 209 to provide an indication of the emotional state of the user to others in the environment of the user. Feedback unit 209 would typically also provide some biofeedback to the user, but since its primary use according to this aspect of the present invention is to indicate the emotional state of the user to others, unit 209 will be referred to as an indicator unit. Additional methods of measuring emotional state of the user can be combined with the apparatus such as galvanic skin response, heart rate.

Preferably indicator unit 209 is configured to project coloured light towards others in the environment of the user and is therefore preferably provided on the surfaces of the glasses that face outwards, away from the face of the user. Most preferably the indicator unit is a diffuse light source extending along frame 201 and optionally at least partially along arms 210.

It is advantageous if the emotional state of the user is expressed to others as different colours. This can be achieved by configuring the control unit to cause the indicator unit to emit different colours in dependence on the different facial expressions detected by the biosensors.

As used herein, the terms set and subset refer to one or more items.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. An apparatus for providing muscular biofeedback, comprising:
   facewear supporting biosensors arranged such that, in use, the biosensors are situated for detecting activity of a predetermined set of facial muscles;
   a feedback unit integral with the facewear for providing biofeedback to a wearer of the facewear; and
   a control unit coupled to the biosensors and the feedback unit and arranged to identify patterns in the signals from the biosensors characteristic of one or more predefined imbalances in muscle activity between the left and right sides of the face; wherein the control unit is configured to identify a pattern in the signals from the biosensors characteristic of a first predefined imbalance in muscle activity between the left and right sides of the face by comparing the activity of predetermined corresponding facial muscles on the left and right sides of the face, and responsive to identifying the first predefined imbalance, cause the feedback unit to provide different biofeedback to each side of the face in correspondence with the first predefined imbalance, the biofeedback provided to a particular side of the face being provided only to that respective side of the face.

2. The apparatus as claimed in claim 1, wherein the facewear comprises eyewear and the feedback unit comprises corrective or non-corrective lenses arranged so as to in use be located over the eyes of the wearer, the lenses being configured to provide visual biofeedback by means of changes in the color or transmittance of one or both of the lenses.

3. The apparatus as claimed in claim 1, wherein the predetermined set of facial muscles includes the posterior auricular muscle and the control unit is configured to infer the activity of a zygomaticus muscle from the activity of the posterior auricular muscle on the same side of the face.

4. The apparatus as claimed in claim 3, wherein the control unit is configured to identify a pattern in the signals from the biosensors characteristic of a first predefined facial expression and to, on identifying the pattern in the signals from the biosensors characteristic of the first predefined facial expression, cause the feedback unit to provide biofeedback indicative of the first predefined facial expression.

5. The apparatus as claimed in claim 1, wherein the control unit is configured to identify that the pattern in the signals from the biosensors is characteristic of the first predefined imbalance in muscle activity if the signals from the biosensors indicate that the asymmetry between the activity of the predetermined corresponding facial muscles on the left and right sides of the face exceeds a predetermined threshold for at least a predetermined minimum duration.

6. The apparatus as claimed in claim 5, wherein, if the duration of time when the control unit causes the feedback unit to provide biofeedback falls below a predetermined duration, the control unit is configured to automatically decrease the predetermined threshold.

7. The apparatus as claimed in claim 5, wherein the control unit is configured to store information defining which side of the face the first predefined imbalance is primarily associated with and to, in use, provide biofeedback at least primarily to that defined side of the face.

8. The apparatus as claimed in claim 5, wherein, if the frequency of occurrence of periods of time when the control unit causes the feedback unit to provide biofeedback falls below a predetermined frequency of occurrence, the control unit is configured to automatically decrease the predetermined threshold.

9. The apparatus as claimed in claim 5, wherein the control unit is configured to provide one or more of visual, auditory or vibrational biofeedback to the eye or ear of each side of the face in correspondence with the first predefined imbalance.

* * * * *